(12) United States Patent
Wang et al.

(10) Patent No.: US 11,903,735 B2
(45) Date of Patent: Feb. 20, 2024

(54) APPARATUS OF EXAMINING SURFACE OF AN ORGANISM AND METHOD THEREOF

(71) Applicants: Hsin-Yao Wang, Chiayi (TW); Ting-Wei Lin, Taoyuan (TW); Jang-Jih Lu, Taoyuan (TW)

(72) Inventors: Hsin-Yao Wang, Chiayi (TW); Ting-Wei Lin, Taoyuan (TW); Jang-Jih Lu, Taoyuan (TW)

(73) Assignees: CHANG GUNG UNIVERSITY, Taoyuan (TW); CHANG GUNG MEMORIAL HOSPITAL, LINKOU, Taoyuan (TW)

(*) Notice: Subject to any disclaimer, the term of this patent is extended or adjusted under 35 U.S.C. 154(b) by 72 days.

(21) Appl. No.: 17/245,873

(22) Filed: Apr. 30, 2021

(65) Prior Publication Data

US 2022/0031247 A1 Feb. 3, 2022

(30) Foreign Application Priority Data

Jul. 28, 2020 (TW) ................................. 109125374

(51) Int. Cl.
*A61B 5/1477* (2006.01)
*A61B 5/00* (2006.01)
*A61B 5/145* (2006.01)

(52) U.S. Cl.
CPC .......... *A61B 5/6833* (2013.01); *A61B 5/1477* (2013.01); *A61B 5/14546* (2013.01); *A61B 5/4866* (2013.01); *A61B 2562/028* (2013.01)

(58) Field of Classification Search
CPC . A61B 5/6833; A61B 5/14546; A61B 5/1477; A61B 5/4866; A61B 1462/028
See application file for complete search history.

(56) References Cited

U.S. PATENT DOCUMENTS

| 2011/0160069 A1* | 6/2011 | Corrie ............................... 506/7 |
| 2013/0115685 A1* | 5/2013 | Holmes .............. A61B 5/15142 422/68.1 |
| 2013/0137054 A1* | 5/2013 | Jiang ..................... C08F 220/54 137/67 |
| 2013/0210991 A1* | 8/2013 | Fonnum ................ C08F 257/02 524/547 |
| 2013/0280696 A1* | 10/2013 | Millenson .......... A61B 5/14546 435/5 |
| 2019/0142642 A1* | 5/2019 | Burnet ..................... A61L 15/38 600/362 |
| 2020/0155048 A1* | 5/2020 | Bertand ............. A61B 5/14546 |
| 2021/0223234 A1* | 7/2021 | Fitzgerald .......... G01N 33/5438 |
| 2021/0338195 A1* | 11/2021 | Reiche ................... A61B 90/39 |
| 2022/0015688 A1* | 1/2022 | Larson ................. A61B 5/1468 |

* cited by examiner

*Primary Examiner* — Puya Agahi
*Assistant Examiner* — Grace L Rozanski

(57) ABSTRACT

An apparatus and method for examining an organism surface includes a pliable member including a contact layer, a plurality of channels, and a reaction layer, wherein the plurality of channels are disposed between the contact layer and the reaction layer; each of the channels having a size in the range of micrometers and formed of biocompatibility materials, and the contact layer including a plurality of spherical projections having a size in the range of micrometers and formed of biocompatible materials, and the reaction layer including examining molecules and a reaction unit.

7 Claims, 5 Drawing Sheets

Adhering a plurality of spherical projections for examination of a pliable member to a surface of an organism, wherein the spherical projections for examination collect secreted fluid of the organism, and the secreted fluid has a substance to be analyzed. — S1

Flowing the secreted fluid to a contact layer through the spherical projections for examination and flowing the secreted fluid from the contact layer to a reaction layer through a plurality of channels, so that a target substance of the substance to be analyzed reacts with examining molecules and a reaction unit in the reaction layer, thereby determining health or illness of the organism based on visible changes of the reaction unit and achieving a purpose examining the surface of the organism. — S2

FIG. 5

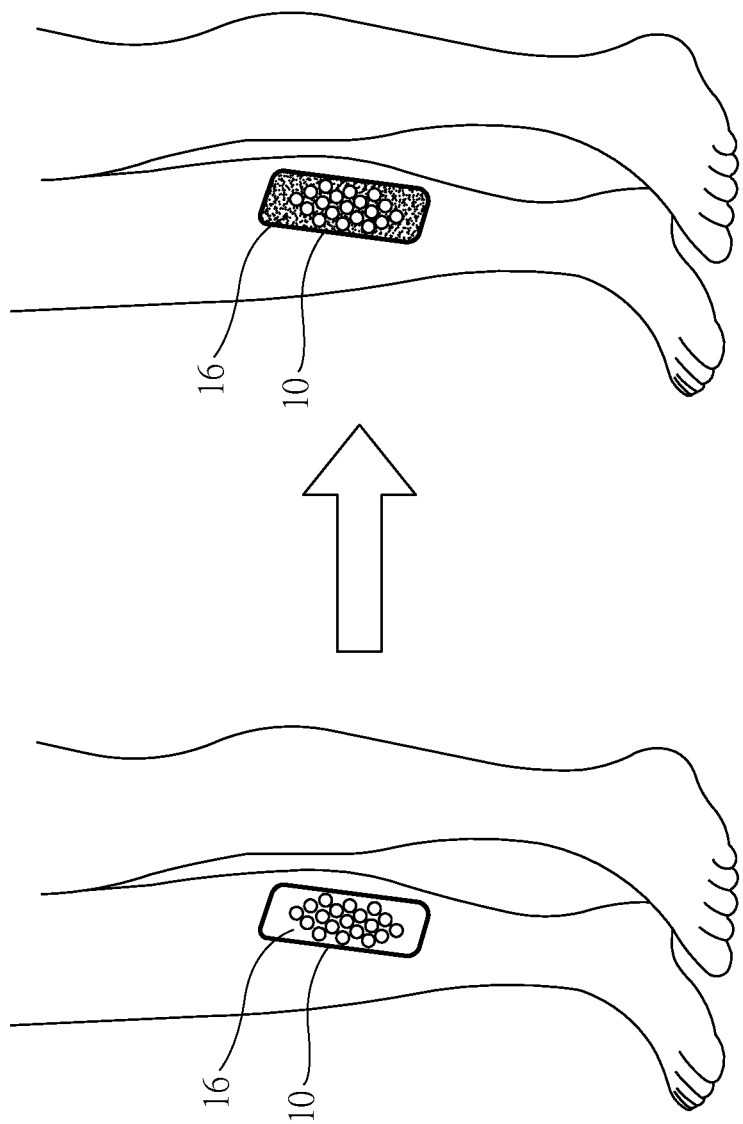

US 11,903,735 B2

APPARATUS OF EXAMINING SURFACE OF AN ORGANISM AND METHOD THEREOF

BACKGROUND OF THE INVENTION

1. Field of the Invention

The invention relates to examination apparatuses and methods and more particularly to an apparatus of examining health status of an organism and method thereof by adhering a pliable member to a surface of the organism, utilizing projection array for examination, collecting body fluid of the organism and flowing same to a reaction layer, examining a target substance of the collected fluid from the organism, and changing color of a reaction layer or emitting fluorescence.

2. Description of Related Art

Conventionally, blood is taken as a target substance for examining health of an organism. However, this method is invasive and the organism may feel pain and discomfort due to a collection procedure. Further, subsequent examination procedures are tedious and time consuming. Moreover, repeated blood drawing is often needed for longitudinal monitoring. Furthermore, blood testing is often less sensitive to localize soft tissue infection or inflammation.

For solving above problems, a conventional method comprises the steps of applying a dressing patch on a surface of the organism, and activating a sensor in the dressing patch to examine a metabolic substance (or a volatile organic substance formed by degradation) in an exudate fluid from skin lesions of the organism. However, the conventional method is limited in applications. For example, it collects the exudate fluid in a passive way. That is, the conventional method is useless if the organism has intact skin. Further, the target substance is required to be a metabolic substance (or a volatile organic substance formed by degradation) in the exudate fluid from the skin lesions of the organism. Thus, the conventional method is impossible of examining the organism under above condition.

Therefore, the need for improvement still exists.

SUMMARY OF THE INVENTION

It is therefore one object of the invention to provide an apparatus of examining through surface of an organism, comprising a pliable member including a contact layer, a plurality of channels, and a reaction layer; wherein the channels are disposed between the contact layer and the reaction layer; the channels have a size in the range of micrometers and are formed of biocompatibility materials; the contact layer includes a plurality of spherical projections for examination having a size in the range of micrometers and being formed of biocompatibility materials; and the reaction layer includes examining molecules and a reaction unit.

It is another object of the invention to provide a method of examining surface of an organism, comprising the steps of adhering a plurality of spherical projections for examination of a pliable member to a surface of an organism by applying a predetermined pressure wherein the spherical projections for examination have a size in the range of micrometers and are formed of biocompatibility materials so that the spherical projections for examination are able to collect fluid of the organism as a collected fluid, and the collected fluid has a substance to be analyzed; and flowing the collected fluid to a contact layer through the spherical projections for examination; flowing the collected fluid from the contact layer to a reaction layer through a plurality of channels wherein the channels have a size in the range of micrometers and are formed of biocompatibility materials so that a target substance of the substance to be analyzed reacts with examining molecules and a reaction unit in the reaction layer, thereby determining health or illness of the organism based on visible changes of the reaction unit and achieving a purpose examining the surface of the organism.

The invention has the following advantages and benefits in comparison with the conventional art:

Regarding the examination on the surface of the organism, the pliable member is adhered to the surface of the organism to absorb the fluid collected from the organism, thereby achieving the purpose of examining the health or illness of the organism in a painless manner.

Regarding collecting the fluid, the spherical projections for examination have a size in the range of micrometers and thus a patient does not feel any pain when the spherical projections are pressed into the surface of the organism. Further, the biocompatibility materials are hydrophilic and can absorb fluid pressed out from the surface of the organism, thereby achieving the purpose of collecting the fluid under the surface of the organism.

Regarding examining a non-volatile organic substance, the pliable member can examine not only a volatile organic substance but also the non-volatile organic substance because the reaction layer includes the examining molecules and the reaction unit.

Regarding determining examination results, it is possible of determining whether the organism is healthy or ill based on color change of the reaction layer or fluorescence emission. This is because the examining molecules can recognize a nuclei acid fragment of the target substance in the collected fluid, and the nuclei acid fragment of the target substance binds the reaction unit to cause a reaction on a surface of the reaction layer.

The above and other objects, features and advantages of the invention will become apparent from the following detailed description taken with the accompanying drawings.

BRIEF DESCRIPTION OF THE DRAWINGS

FIG. 5 is a flow chart of a method of examining surface of an organism in accordance with the invention; and FIG. 6 is an environmental view showing an embodiment of the invention.

DETAILED DESCRIPTION OF THE INVENTION

Figure 1:
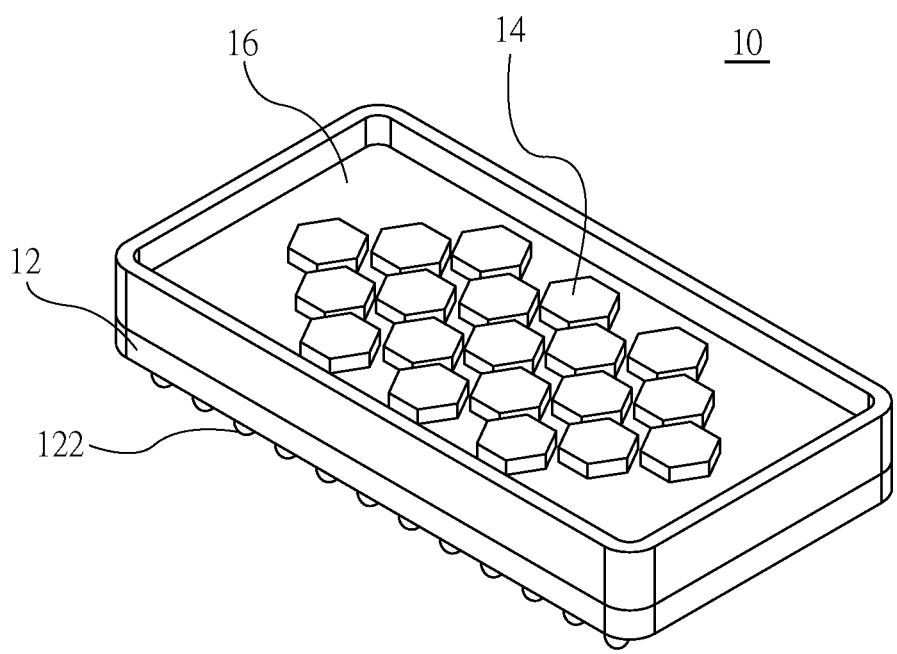
FIG. 1 is a perspective view of an apparatus of examining surface of an organism according to the invention.
Figure 2:
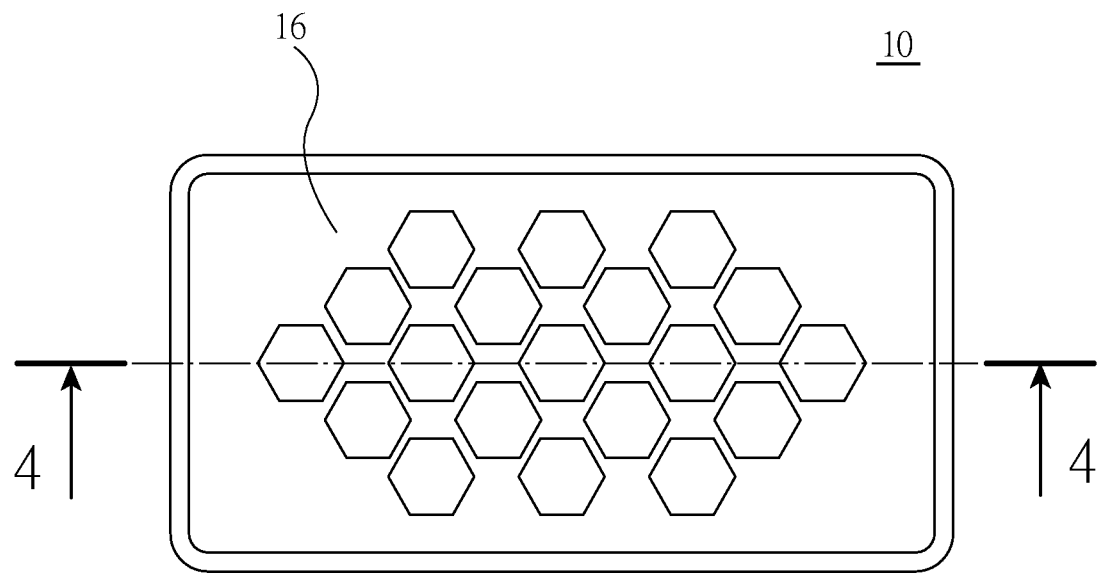
FIG. 2 is a top plan view of FIG. 1.

Referring to FIGS. 1 to 4, an apparatus of examining surface of an organism in accordance with the invention is implemented as a pliable member 10 and comprises a contact layer 12, a plurality of channels 14 and a reaction layer 16 as detailed below.

The channels 14 are disposed between the contact layer 12 and the reaction layer 16. The contact layer 12 includes a plurality of spherical projections 122 for examination having a size in the range of micrometers and being formed of biocompatibility materials. The reaction layer 16 includes examining molecules and a reaction unit. The examining molecules are specific apoenzyme, deoxyribonucleic acid (DNA), single-strand binding protein, primers for reactants, polymeric apoenzyme or monomeric nuclei acid. The reaction unit is a molecular beacon, color protein, fluorescent protein or an electro-magnetic signal. It is possible of determining health or disease of the organism based on the color change or emitted fluorescence. The disease means metabolic disease, cancer, contagious disease including bacteria infection or virus infection.

Figure 3:
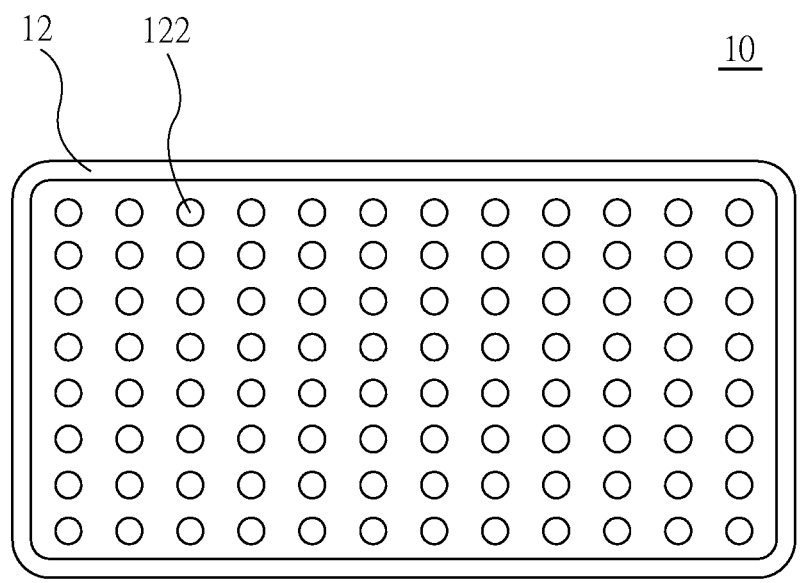
FIG. 3 is a bottom plan view of FIG. 1.
Figure 4:
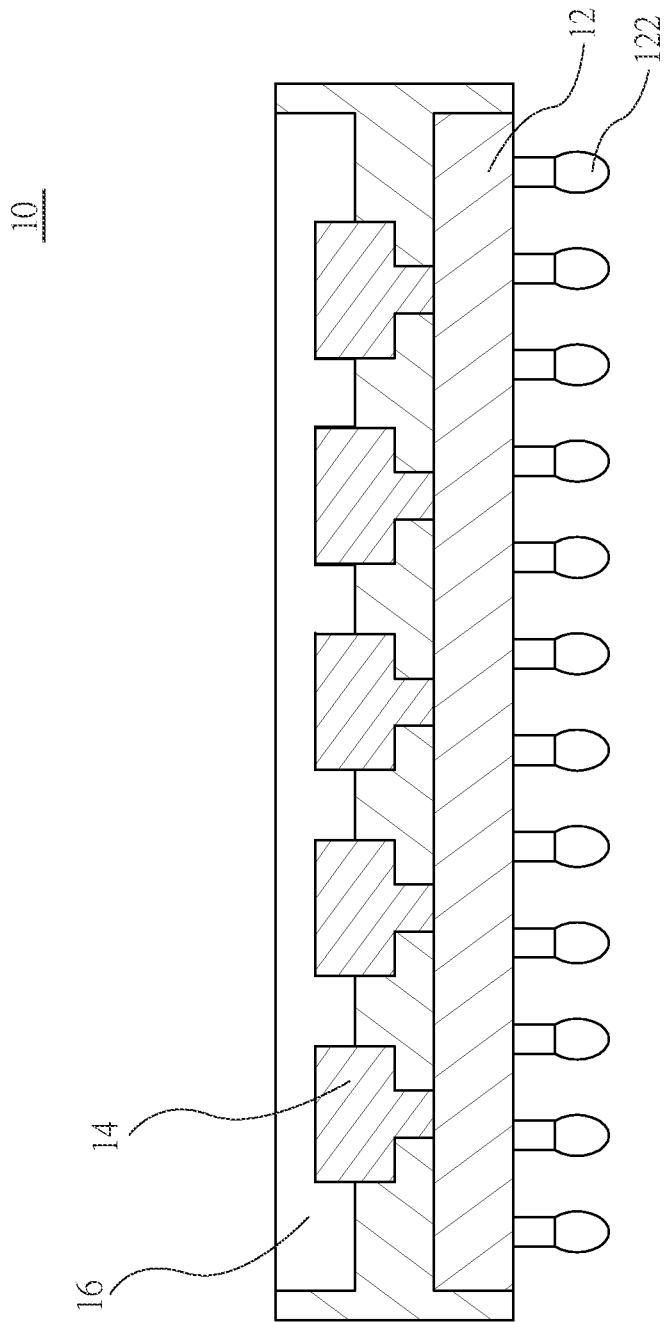
FIG. 4 is a sectional view taken along line 4-4 of FIG. 2.

As shown in FIGS. 3 and 4 specifically, the spherical projection for examination 122 has a diameter of 100-500 μm and is formed of biocompatibility materials which are multiple layered polymer and hydrophobic or hydrophilic. Further, the biocompatibility materials have properties of absorbing fluid.

For the biocompatibility materials contacting the skin are hydrophobic, the spherical projections 122 for examination having the size in the range of micrometers forms a plurality of micro-channels of 30-80 μm wide. Taking advantage of the hydrophobic property, secreted fluid may flow to the spherical projections 122 for examination due to capillary action or by using a micro pump. The hydrophobic materials are polymerized by multiple repeating acrylate having biocompatibility and composed of isobornyl acrylate, 1,10-decanediol diacrylate, pentaerythritol tetraacrylate or acrylate oligomer of different composition ratios. For the hydrophobic materials polymerized by multiple repeating acrylate, they are polymerized by pentaerythritol tetraacrylate and acrylate oligomer in a ratio ranged from 2:1 to 1:1. The higher ratio of acrylate oligomer, the strength and the hardness of bonds of its polymer increase.

For the biocompatibility materials contacting the skin are hydrophilic, the spherical projection 122 for examination formed of the biocompatibility materials having the size in the range of micrometers is formed of hydrogel which has a property of absorbing the secreted fluid. Hydrogel is formed by polymerizing multiple hydrophilic monomers in a ratio ranged from 100:1 to 1:1. For example, hydrogel is composed of methyl vinyl ether/maleic anhydride copolymer having a ratio of 10-12% and polyethylene glycol having a ratio of 4-7%. For example, hydrogel is also composed of methyl vinyl ether/maleic anhydride copolymer and polyethylene glycol in a ratio ranged from 2:1 to 2.5:1. For example, hydrogel is still composed of polyvinyl alcohol and chitosan in a ratio ranged from 100:1 and 50:50. The higher ratio of chitosan, the higher porosity thereof is. For example, hydrogen is yet composed of polyethylen glycol diacrylate and phenylbis (2,4,6-trimethylbenzoyl) phosphine oxide having a ratio ranged from 100:1 to 20:1.

Referring to FIG. 5 in conjunction with FIGS. 1 to 4, a flow chart of a method of examining surface of an organism in accordance with the invention is illustrated. The method comprises the following steps:

S1 doing a simple cleaning on a surface of an organism to be examined; adhering the plurality of spherical projections 122 for examination of the pliable member 10 to the surface of the organism by applying a predetermined pressure thereon; and utilizing the spherical projections 122 for examination on the surface of the organism in which the spherical projections 122 for examination have a size in the range of micrometers and are formed of biocompatibility materials so that the spherical projections 122 for examination can be pressed into the surface of the organism without causing pain to a patient. The spherical projections 122 for examination are capable of collecting fluid of the organism as a collected fluid. The collected fluid is mainly from interstitial parts of the organism or fluid secreted from a wound and has a substance adapted to be analyzed. Further, a local swollen area occurs on the surface of the organism when the organism with local inflammation. The swelling increases both pressure and temperature on the local area of the surface of the organism. And in turn, the collected fluid of the organism quickly enters the contact layer 12 of the pliable member 10 through the spherical projections 122 for examination.

S2 flowing the collected fluid to the contact layer 12 through the spherical projections 122 for examination; flowing the collected fluid from the contact layer 12 to the reaction layer 16 through the channels 14 in which the channels 14 have a size in the range of micrometers and are formed of biocompatibility materials so that a target substance of the substance to be analyzed reacts with examining molecules and a reaction unit in the reaction layer 16. A physician can determine health or illness of the organism based on visible changes of the reaction unit, thereby achieving the purpose examining the surface of the organism. The target substance of the substance to be analyzed is protein, nucleic acid, or metabolic molecules. The reaction unit is a molecular beacon, color protein, fluorescent protein or an electro-magnetic signal.

For the target substance of the substance to be analyzed being nucleic acid, examination is made by any one of or any combination of aptamer, deoxyribozyme, cell-free protein expression system, enzyme-involed colorimetric methods, isothermal nucleic acid amplification detection, constant temperature nuclei acid amplification, catalytic nucleic acid mediated amplification or other enzyme-involved reaction. In case of constant temperature nuclei acid amplification being used, in a temperature condition of 37° C.-42° C. the reaction layer 16 includes the above examining molecules and the reaction unit in which specific apoenzyme in the body fluid to be examined is used by the examining molecules. The specific apoenzyme includes enzyme having biopolymeric functions, single-strand binding protein, and re-sequenced enzyme for binding a specific sequence. The specific apoenzyme can achieve the purposes of identifying a specific sequence and amplifying a nuclei acid fragment. Thus, the above examining molecules and primers approach a specific deoxyribonucleic acid (DNA) fragment of the target substance in the collected fluid, thereby amplifying the DNA fragment in a target area of the target substance and binding the reaction unit to change color of a surface of the reaction layer 16 or emit fluorescence.

The examining molecules are specific apoenzyme, DNA, single-strand binding protein, primers for reactants, polymeric apoenzyme or monomeric nuclei acid. Thus, the examination method of the invention has wide applications.

The reaction unit is a molecular beacon, color protein, fluorescent protein or an electro-magnetic signal.

For the reaction unit being molecular beacon, the nuclei acid fragment of the above target substance is required to bind the molecular beacon to change color of the molecular beacon.

For the reaction unit being fluorescent protein, visible light is emitted in a predetermined period of time by waves having a predetermined wavelength.

For the target substance of the substance to be analyzed being protein, any one of or any combination of aptamer, deoxyribozyme, cell-free protein expression system, enzyme-involed colorimetric methods or isothermal nucleic acid amplification detection is used for examination.

For the target substance of the substance to be analyzed being metabolic molecules, any one of or any combination of aptamer, deoxyribozyme, cell-free protein expression system, enzyme-involed colorimetric methods or isothermal nucleic acid amplification detection is used for examination.

Further, the micrometric elements of the biocompatibility materials in the channels 14 can absorb excessive substance of the substance to be analyzed. The excessive substance is protein, lipid, carbohydrates or magnesium ion. Thus, the number of non-examination targets in the reaction layer 16 is decreased, thereby adjusting composition ratios of the biocompatibility materials, changing absorbed substance after the channels 14 have absorbed the secreted fluid, filtering out different composition, and finally changing examination sensitivity and peculiarity.

Referring to FIG. 6 in conjunction with FIGS. 1-4, an embodiment of the invention is shown by taking examination of no-wound cellulitis as an exemplary example of the apparatus of examining organism surface and method thereof. In the embodiment, the leg cellulitis caused by *Staphylococcus aureus* is examined. First, the leg is suspected to have local inflammation but with no obvious surface lesion. Next, the surface of the leg is pasteurized and cleaned. Next, the pliable member 10 is adhered to the swollen area of the leg of a patient. The spherical projections 122 for examination of the contact layer 12 collect the fluid pressed out from the swollen area. Advantageously, the patient does not feel pain or discomfort in the process. The collected fluid flows from the channels 14 to the reaction layer 16 through the spherical projections 122 for examination. The specific examining molecules and the reaction unit in the reaction layer 16 tries to catch the possible pathogen from the collected fluid. It is determined that the leg cellulitis is caused by certain bacteria if there is color change on the surface of the reaction layer 16. Otherwise, it is determined that the leg is not infected by pathogens if there is no color change on the surface of the reaction layer 16.

While the invention has been described in terms of preferred embodiments, those skilled in the art will recognize that the invention can be practiced with modifications within the spirit and scope of the appended claims.

What is claimed is:

1. A method of examining a surface of an organism, comprising steps of:
   providing a pliable member having a contact layer, a reaction layer, and a plurality of channels, wherein the contact layer has a plurality of spherical projections for examination, wherein the spherical projections have a size in a range of micrometers and are formed of biocompatible materials;
   adhering the spherical projections to the surface of the organism by applying a predetermined pressure, wherein the spherical projections continuously collect fluid of the organism as a collected fluid from the surface of the organism by capillary action or by using a micro pump, wherein the spherical projections do not puncture the surface of the organism, wherein the collected fluid is from interstitial parts of the organism or fluid secreted from a wound of the organism, and wherein the collected fluid has a substance to be analyzed;
   continuously flowing the collected fluid to the contact layer through the spherical projections; and
   continuously flowing the collected fluid from the contact layer to the reaction layer through the plurality of channels wherein the channels have a size in the range of micrometers and are formed of biocompatible materials, wherein a target substance of the substance to be analyzed reacts with examining molecules, wherein the examining molecules are specific apoenzyme, deoxyribonucleic acid (DNA), single-strand binding protein, primers for reactants, polymeric apoenzyme or monomeric nuclei acid, and a reaction unit in the reaction layer, wherein the reaction unit is a molecular beacon, color protein, fluorescent protein or an electro-magnetic signal, thereby providing an indication of health or illness of the organism based on visible changes of the reaction unit,
   wherein micrometric elements of the biocompatible materials of the channels absorb excessive substance of the substance to be analyzed and a number of non-examination targets in the reaction layer is decreased, thereby adjusting composition ratios of the biocompatible materials, changing absorbed substance after the channels have absorbed the excessive substance of the substance to be analyzed, and changing examination sensitivity and peculiarity, wherein the biocompatible materials are hydrophobic or hydrophilic,
   wherein when the biocompatible materials are hydrophobic, the collected fluid passing the spherical projections for examination having the size in the range of micrometers form a plurality of micro-channels of 30-80 μm wide, and the hydrophobic biocompatible materials are polymerized by multiple repeating acrylate having biocompatibility and composed of isobornyl acrylate, 1,10-decanediol diacrylate, pentaerythritol tetraacrylate or acrylate oligomer of different composition ratios, and
   wherein when the biocompatible materials comprise hydrophilic formed of hydrogel, the hydrogel has a property of absorbing the collected fluid and is formed by polymerizing multiple hydrophilic monomers in a ratio ranging from 100:1 to 1:1.

2. The method of claim 1, wherein when the target substance of the substance to be analyzed comprises protein, any one of or any combination of aptamer or deoxyribozyme is used for examination.

3. The method of claim 1, wherein when the target substance of the substance to be analyzed comprises protein, any one of or any combination of cell-free protein expression system, enzyme-involed colorimetric methods or isothermal nucleic acid amplification detection is used for examination.

4. The method of claim 1, wherein when the target substance of the substance to be analyzed comprises nucleic acid, any one of or any combination of aptamer or deoxyribozyme is used for examination.

5. The method of claim 1, wherein when the target substance of the substance to be analyzed comprises nucleic acid, any one of or any combination of cell-free protein expression system, enzyme-involed colorimetric methods or isothermal nucleic acid amplification detection is used for examination.

6. The method of claim 1, wherein when the target substance of the substance to be analyzed comprises metabolic molecules, any one of or any combination of aptamer or deoxyribozyme is used for examination.

7. The method of claim 1, wherein when the target substance of the substance to be analyzed comprises metabolic molecules, any one of or any combination of cell-free protein expression system, enzyme-involed colorimetric methods or isothermal nucleic acid amplification detection is used for examination.

* * * * *